US009639325B2

(12) United States Patent
Dziedzicki et al.

(10) Patent No.: US 9,639,325 B2
(45) Date of Patent: May 2, 2017

(54) FINDING A BEST MATCHING STRING AMONG A SET OF STRINGS

(71) Applicant: International Business Machines Corporation, Armonk, NY (US)

(72) Inventors: Tomasz Dziedzicki, Lomza (PL); Marek J. Kiszkis, Warsaw (PL); Grzegorz Kokosinski, Warsaw (PL); Krzysztof Zarzycki, Warsaw (PL)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 213 days.

(21) Appl. No.: 14/372,481

(22) PCT Filed: Feb. 19, 2013

(86) PCT No.: PCT/IB2013/051345
§ 371 (c)(1),
(2) Date: Jul. 16, 2014

(87) PCT Pub. No.: WO2013/128333
PCT Pub. Date: Sep. 6, 2013

(65) Prior Publication Data
US 2015/0026194 A1    Jan. 22, 2015

(30) Foreign Application Priority Data
Mar. 1, 2012  (EP) .................................... 12157802

(51) Int. Cl.
G06F 17/30   (2006.01)
G06F 7/24    (2006.01)
G06F 19/26   (2011.01)

(52) U.S. Cl.
CPC .......... *G06F 7/24* (2013.01); *G06F 17/30663* (2013.01); *G06F 17/30985* (2013.01); *G06F 19/26* (2013.01); *G06F 2207/228* (2013.01)

(58) Field of Classification Search
None
See application file for complete search history.

(56) References Cited

U.S. PATENT DOCUMENTS 6,542,896 B1 *  4/2003  Gruenwald ....... G06F 17/30569
6,792,423 B1    9/2004  Jeffries et al.
(Continued)

FOREIGN PATENT DOCUMENTS

CN    1461444 A    12/2003
CN    1983249 A    6/2007

OTHER PUBLICATIONS

Farivar et al., "Accurate Sequence Alignment using Distributed Filtering on GPU Clusters", Technical Report, Ideals, University of Illinois; 2011; pp. 1-9.

(Continued)

*Primary Examiner* — Jay Morrison
(74) *Attorney, Agent, or Firm* — Cantor Colburn LLP; Ed Choi

(57) ABSTRACT

A method for finding a best matching string among a set of strings for a reference string includes representing, for each of the set of strings paired with the reference string, a dynamic programming problem for calculating a final alignment score as a matrix of cells, and calculating a current optimal alignment boundary threshold. The method also includes executing, for each string of the set of strings, a calculation of a prospective final alignment score of a candidate alignment of the each of the set of strings and the reference string for each cell. Based on determining, that prospective final alignment score improves the current optimal alignment boundary threshold, the method includes calculating a final alignment score for the string of the set of strings associated with the cell. Otherwise, the method includes aborting the calculation of a candidate alignment covering the string associated with the cell.

12 Claims, 5 Drawing Sheets

(56) References Cited

U.S. PATENT DOCUMENTS

| | | | |
|---|---|---|---|
| 2009/0265303 A1 | 10/2009 | Parikh et al. | |
| 2010/0070200 A1* | 3/2010 | Sarikaya | G06F 19/22 702/30 |
| 2010/0138376 A1* | 6/2010 | Avis | G06F 17/30985 706/50 |
| 2010/0257172 A1 | 10/2010 | Lambert et al. | |

OTHER PUBLICATIONS

Galgonek et al., SProt: sphere-based protein structure similarity algorithm: Proteome Science 2011 9 (Suppl 1): S20, published Oct. 14, 2011; BioMed Central; http://www.proteomesci.com/content/9/S1/S20; pp. 1-12.

International Search Report for International Application No. PCT/IB2013/051345; International Filing Date: Feb. 19, 2013; mailing date Jul. 25, 2013; 3 pages.

Ligowski et al., "An Efficient Implementation of Smith Waterman Algorithm on GPU using CUDA, for Massively Parallel Scanning of Sequence Databases", 2009 IEEE, Parallel & Distributed Processing (IPDPS), May 23-29, 2009, Rome; pp. 1-8.

Chinese Office Action for CN201380011914.1; mailed Oct. 11, 2016; 5 pgs.

\* cited by examiner

FINDING A BEST MATCHING STRING AMONG A SET OF STRINGS

CROSS-REFERENCE TO RELATED APPLICATION

This is a U.S. National Stage of Application No. PCT/IB2013/051345; filed on Feb. 19, 2013; and assigned International Publication No. WO2013128333 A1; published on Sep. 6, 2013, which claims priority to European Patent Application No. 12157802.5; filed Mar. 1, 2012, the contents of each application in their entirety are herein incorporated by reference.

BACKGROUND

The invention relates to the field of data processing, and more particularly to the field of dynamic programming.

The problem of finding a best matching string and a corresponding optimal alignment score out of a set of strings (typically stored in a database) in respect to a reference string (or 'query string') is a common problem in many fields of technology, in particular in the field of bioinformatics and text analysis. Various sequence alignment algorithms for aligning two or more biological sequences, e.g. protein-, DNA- or RNA-sequences, are known and can be used e.g. for determining evolutionary conserved sequence homologies, for determining text documents stored in databases or the Internet which are highly similar to a reference text.

Sequence (or 'string') alignment algorithms are computationally complex. Most alignment programs use heuristic methods rather than global optimization because identifying the optimal alignment between more than a few sequences of moderate length is prohibitively computationally expensive. However, heuristic approaches increase the processing speed at the cost of accuracy. Thus, it is not guaranteed that an optimal alignment will be found. Other approaches such as, for example, dynamic programming approaches (e.g. based on an ordinary Needleman-Wunsch or Smith-Waterman algorithms) guarantee to give the correct and optimal sequence alignment as a result. However, said exact approaches are still too slow for many multiple sequence alignment problems of high complexity, even when performed on a graphical processing unit (GPU), as in the computational cost of a pairwise sequence alignment is quadratic with regard to the sequences' lengths.

However, it is sometimes required to find the exact best match quickly, in particular in medicine and the life sciences where the correctness of an alignment result may be of crucial impact for the diagnosis of a disease or for testing the validity of a scientific hypothesis.

SUMMARY

Embodiments include methods, systems and computer program products for finding a best matching string among a set of strings for a reference string. Aspects include representing, for each of the set of strings paired with the reference string, a dynamic programming problem for calculating a final alignment score as a matrix of cells, each cell representing an intermediate result to be calculated and calculating a current optimal alignment boundary threshold. Aspects further include, for each string of the set of strings, calculating a prospective final alignment score of a candidate alignment of the each of the set of strings and the reference string for each cell. Based on determining that prospective final alignment score improves the current optimal alignment boundary threshold, aspects include calculating a final alignment score for the string of the set of strings associated with the cell. Based on determining that prospective final alignment score does not improve the current optimal alignment boundary threshold, aspects include aborting the calculation of a candidate alignment covering the string of the set of strings associated with the cell.

Additional features and advantages are realized through the techniques of the present disclosure. Other embodiments and aspects of the disclosure are described in detail herein. For a better understanding of the disclosure with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The foregoing and other features, and advantages of the disclosure are apparent from the following detailed description taken in conjunction with the accompanying drawings in which:

DETAILED DESCRIPTION

In the following, like numbered elements in these figures are either similar elements or perform an equivalent function. Elements which have been discussed previously will not necessarily be discussed in later figures if the function is equivalent.

Figure 1:
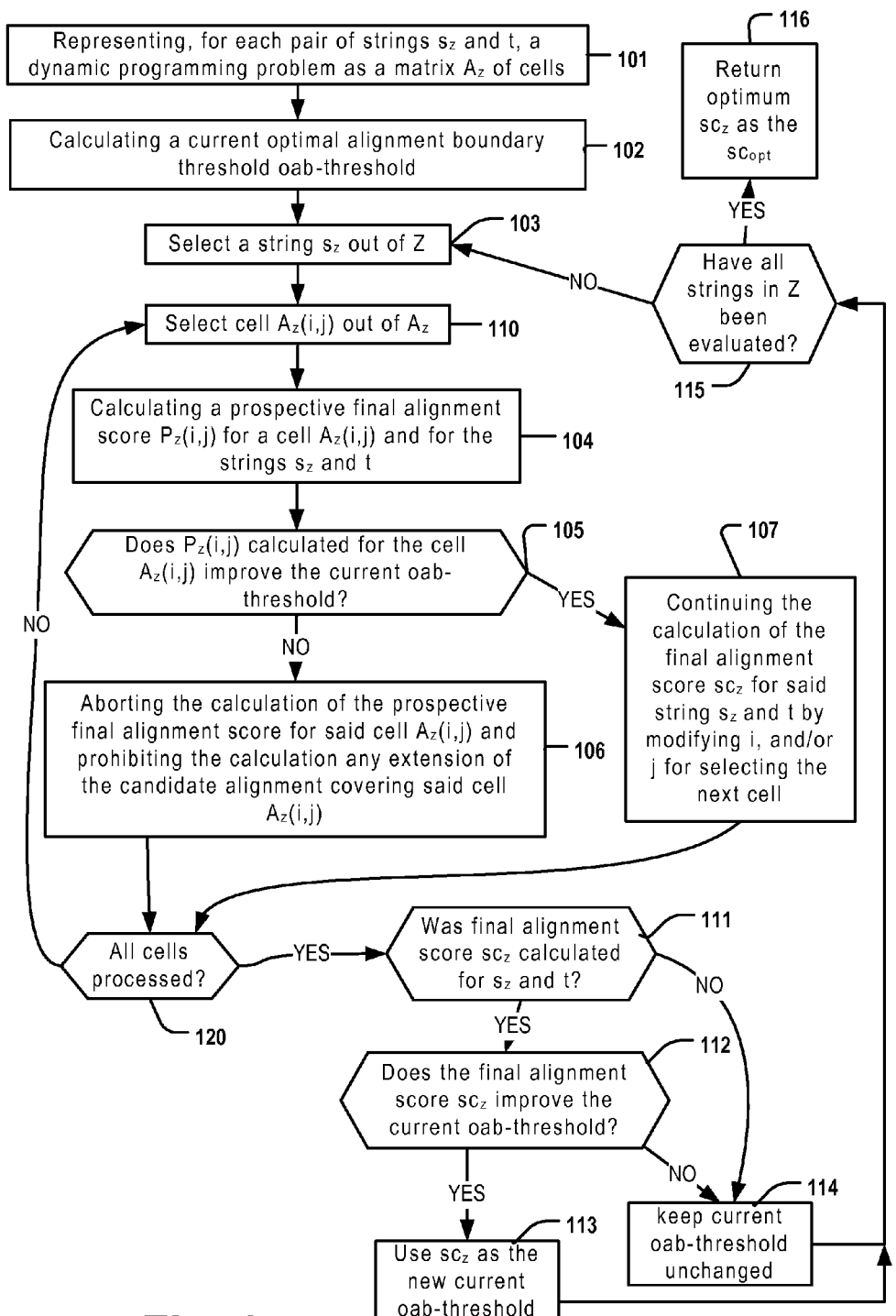
FIG. 1 is a flowchart of a method for finding a best matching string among a set of strings in accordance with an exemplary embodiment.

FIG. 1 shows an embodiment of a method for finding a best matching string sz among a set Z of strings in respect to a reference string t. Reference string t may be a search string while each of the strings of set Z may be a database entry. As shown at block 101, each dynamic programming problem for calculating a final alignment score scz for any pair of strings (sz, t) is represented as a matrix Az of cells. As shown at block 102, an initial current optimal alignment boundary threshold, referred herein as oab-threshold, is calculated. In exemplary embodiments, this calculation may comprise initializing the oab-threshold by an infinite value (respectively+/− infinity for min/max functions) or calculating the oab-threshold based on an approximate final alignment of one of the string pairs. In exemplary embodiments the approximate final alignment score is calculated based on a subset of cells specified by a given parameter K. The approximate final alignment may be calculated by taking only into consideration input provided by cells lying within said sub-set of cells may not be an exact optimum alignment, because it may happen that the real exact optimum alignment lies at least partially out of said subset of cells. However, in particular for similar strings, it will in most of the cases be the exact optimum alignment or at least a good approximation thereof.

As shown at block 103, a string sz is selected from the set Z of strings for calculating the final alignment score for the string pair (sz, t). A first cell, e.g., the left top corner cell of the matrix, may be selected at block 110 to start calculating a prospective final alignment score for the currently selected cell. As shown at block 104, the prospective final alignment score Pz(i, j) is calculated for a candidate alignment of the currently selected string pair (sz, t) and for the selected matrix cell to be covered by said candidate alignment. This calculation comprises the calculation of Fz (i, j). The one matrix cell "divides" the candidate alignment into two sub-alignments whose alignment scores both contribute to the prospective final alignment score but are calculated differently.

As shown at block 105, it is determined if the calculated prospective final alignment score calculated for said particular cell Az(i, j) improves the current oab-threshold. The mathematical meaning of "improve" thereby depends on the question whether the optimization problem being part of the dynamic programming problem is a minimizing or a maximizing function. In case it is determined that the calculated prospective final alignment score does not improve the current oab-threshold, block 106 is executed and the alignment score calculation for the currently selected string sz is aborted. In addition, any extension of the candidate alignment covering said cell Az(i,j) is prohibited, thereby tremendously speeding up the calculation of the final alignment score for the string sz. After having aborted the calculation of the current alignment covering Az(i,j), at block 106, it is determined at block 120 if all cells of the current matrix have been processed. There may exist other alignments of the two strings sz and t not covering said cell Az(i,j), and the cells need to be processed for determining if a more optimum alignment can be obtained. If it is determined at block 120 that all cells of the matrix Az have already been processed, it is determined if a final alignment score was calculated for said two sequences. In case all possible alignments for the current string pair were aborted, it may be determined at block 111 that no final alignment score was calculated and the current optimal alignment score is kept at block 114 unchanged. If it is determined at block 120 that not all cells have been processed, i.e., that there exists the possibility that a more optimal alignment can be found for the two strings, block 110 is executed. As shown at block 110, a cell is selected that was not calculated neither aborted and which is ready for execution (as all input values required are available). In case at block 111 it is determined that the final alignment score was calculated for the two current strings and in case it is determined at block 112 that the final alignment score is more optimal than the current oab-threshold, the determined final alignment score is used as the new oab-threshold. Irrespective if the current oab-threshold is updated or not, in block 115 it is determined if all the strings in Z have already been selected for calculating a respective final alignment score and have finished calculation. Any completely calculated alignment covers the two cells Az(0,0) and Az(N−1, M−1). If this is the case, the optimum one of all calculated final alignment scores scz is returned as the optimum alignment score. If not, another string is selected from the set of strings for calculating an alignment for said other string and t.

In case it is determined at block 105 that the calculated prospective final alignment score does improve the current oab-threshold, block 107 is executed for continuing the calculation of the final alignment score scz for the current string pair by modifying the row and/or column index. This allows the selection of the next cell in block 110 and allows repeating blocks 110, 104, 105, 107, 120 until the intermediate result Fz(i,j) have been calculated for all cells of the matrix Az(i,j) or all the cells have been marked as useless. For example, if an intermediate result has been calculated for Az(i,j), said intermediate result may be used, together with the intermediate results calculated for two other cells, as input for calculating, in a next step, an intermediate result of another cell (for cell Az(i,j), at least the cells Az(i+1,j), Az(i,j+1) and Az(i+1,j+1) must be calculated, if they exist, respectively). In several further iterations of a loop starting with block 110, prospective final alignment scores are calculated analogously until both strings are completely aligned or the calculation of the alignment covering cell Az(i,j) is aborted.

If it is determined at block 111 that the currently calculated intermediate result Fz(i,j) is the final alignment score of the two aligned strings, it is determined at block 112 if said final alignment score improves the current oab-threshold. If so, the current oab-alignment score is replaced in a threshold updating step, as shown at block 113, by the final alignment score scz. If it is determined at block 112 that the final alignment score does not improve the current oab-threshold, the current oab-threshold is kept unchanged in block 114. Then, starting the calculation of the final alignment score is repeated for the other strings from Z until each of the strings in Z has been selected and a corresponding final alignment score scz was returned or until the respective alignment was aborted.

It should be noted that the sequential presentation of the steps does not imply a sequential execution of all steps. According to some embodiments comprising a parallel processing hardware environment having a number of R parallel executable processors or processing units, R strings may be selected from Z and used for the calculation of R alignments in parallel.

If it is determined at block 115 that not all strings in Z have already been selected for calculating a respective final alignment score, a not yet selected string is selected from the set of strings at block 103. The loop starting at block 103 may be continued until for all strings in Z an alignment was calculated or was at least started to be calculated (and later aborted).

After having determined at block 115 that for all strings in Z (or at least for the sequences for which the calculation of the final alignment score was not aborted) the final alignment scores scz was calculated, the optimum final alignment score value (i.e., the minimum final alignment score value for minimizing functions, the maximum final alignment score value for maximizing functions) is returned at block 116 as the optimum alignment score $sc_{opt}$ and the corresponding string sz is considered as the best matching string $s_{opt}$ in respect to string t. The final result is the value of the oab-threshold after all calculations are finished.

Figure 3:
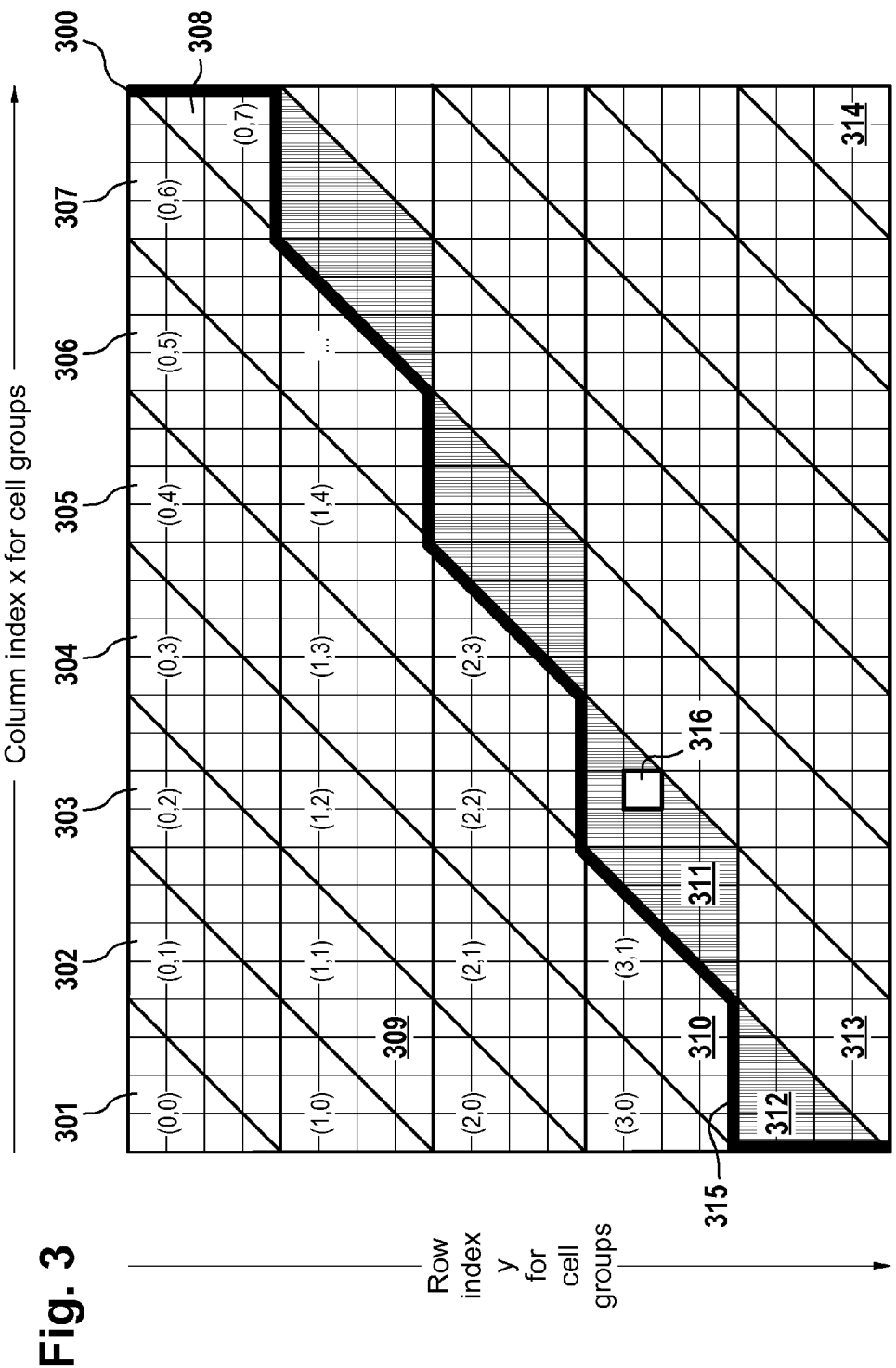
FIG. 3 shows a matrix of cells divided into cell groups in accordance with an exemplary embodiment.

The method steps executed according to FIG. 1 may be executed, at least partially, in parallel. This may be based on calculating an alignment for different pairs of strings in parallel. In addition, or alternatively, the cells of the matrix may be grouped into cell groups as depicted in FIG. 3, whereby the cell groups ready for execution are distributed among a plurality of processing units, e.g. among stream multiprocessing units of a GPU, for parallel executions. Each cell in a cell group may be executed by a respective thread by the respective stream multiprocessor.

Figure 2:
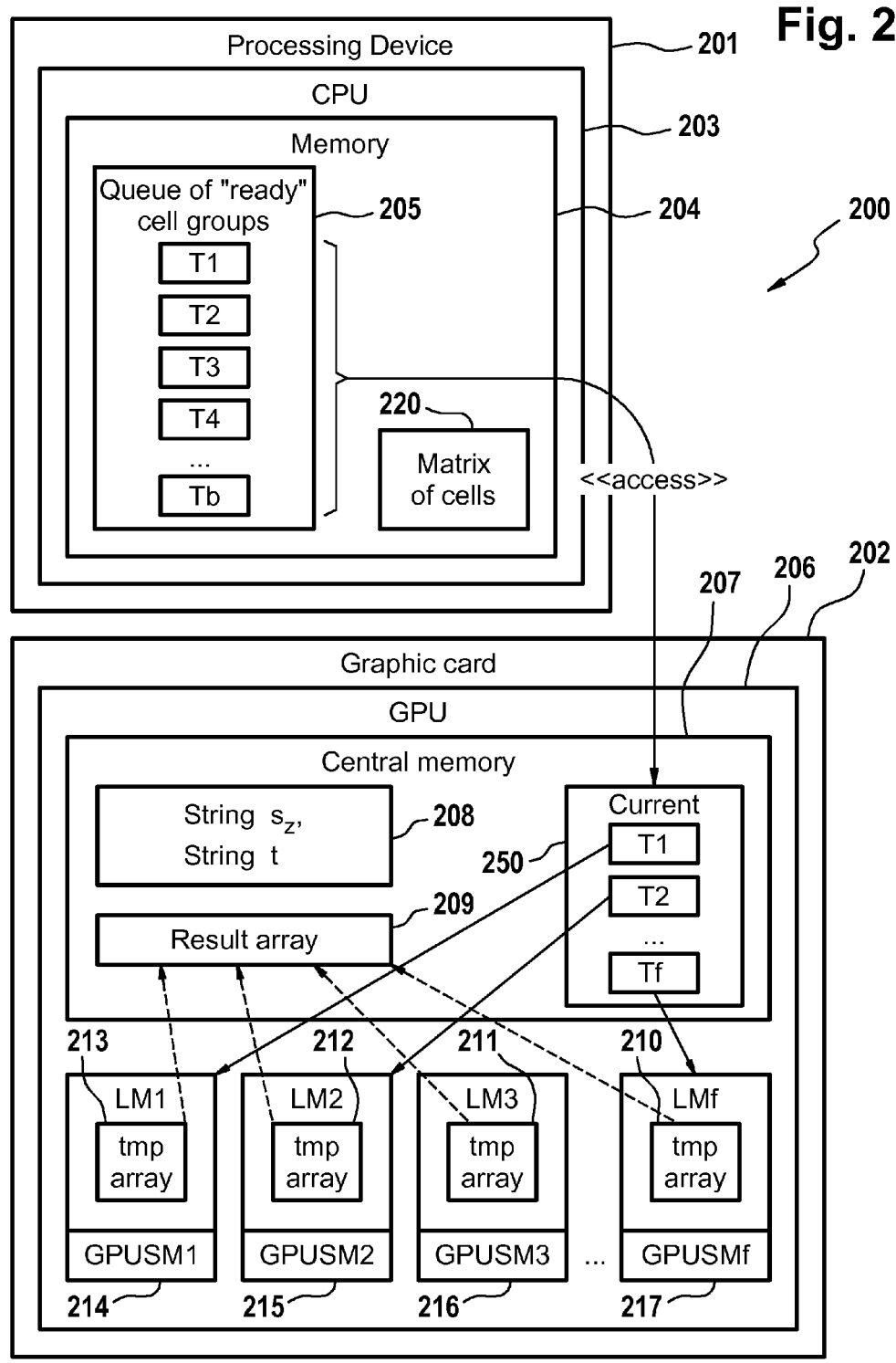
FIG. 2 illustrates a block diagram comprising a first and a second processing unit in accordance with an exemplary embodiment.

FIG. 2 shows a computer system 200 comprising a processing device 201 having a CPU and a memory 204. The memory 204 comprises a FIFO queue comprising at each point in time a plurality of processing tasks T1-Tb. Each of said tasks corresponds to the task of executing a cell group, i.e., executing cells within said group by one of the processing units 214-217 having been assigned to that task. Executing a cell comprises calculating its respective intermediate result Fz (i, j), calculating the prospective final score, and determining at blocks 111, 112 if the calculated intermediate result Fz (i, j) is the final alignment score scz and, if so, if said scz improves the current oab-threshold. The cells belong to a matrix of cells 220 being, according to the depicted embodiment, also stored in memory 204. The processing device 201 may be connected to the other processing device 202, in this case, a graphic card, via a system-internal bus connection.

According to embodiments wherein the computer system 200 comprises a plurality of client computer systems instead of a graphic card 202 (not shown), the central memory 207 is part of a central processing device 201 or is operatively coupled to the central processing device. The central memory would be accessible by each of the client computer systems respectively comprising a multicore processor and respectively comprising a local memory via a network.

Each of the multiple processing units of the depicted embodiment is a stream multiprocessor GPUSM1-GPUSMf of a graphical processing unit 206. Each of the local memories is a shared memory unit LM1, . . . , LMf of one of the stream multiprocessors. The GPU 206 of the graphic card 202 comprises a central memory for storing a result container data structure 209. The central memory also comprises the pair of strings 208 sz and t whose alignment is currently calculated. The central memory further comprises a current data structure 250 for storing as many cell group calculation tasks T1-Tf and corresponding cell groups as processing units 214-217 exist in the GPU 206. Each of the tasks T1-Tf corresponds to one cell group and comprises the task of executing said cell group. The CPU having access to the memory 204 comprising a FIFO queue also has access to the central memory comprising the current data structure 250. The CPU is operable to copy one or more of the cell groups to the current data structure for concurrent execution of the cell groups. Each cell group is distributed from the current data structure 250 to its respectively assigned processing units 215-217. For example, the cell group to be executed in tasks T1 is assigned to processing unit 214. Each stream multiprocessor 214-217, when calculating a cell group, reads the required values from GPU's result container data structure 209. The intermediate results of each cell of said cell group may be stored in a temporary array 213 of the local memory LM1 of the processing units currently executing the cell group. After having calculated all intermediate results for each cell of said cell group, a subset of said intermediate results is selected and copied as the result of said cell group into corresponding array elements of the results container data structure 209. Said subset may comprise at least the lowest cell row of said cell group and the two rightmost cells of each row of said cell group. This copying is indicated by the dotted arrows originating from the local memories LM1-LMf FIG. 3 shows a matrix 300 of cells 316, the cells being grouped into cell groups 301-314 characterized by a column index x and a row index y. Cell group (0, 0) is a triangle-shaped "start" cell, cell group (0,7) is an "end" cell group. The cell groups 302-307 are diamond-shaped cell groups. The thick line 315 originating in the lowest left cell and in the uppermost right cell of the matrix indicates a horizon of cells. The "horizon" is a set of array elements of dimension M+N+1 being mapped to a dynamically changing set of cells of the Matrix Az which represent the "current state" of the dynamic programming function, i.e., represent the "border of knowledge" in the form of left-most and bottom most cells of said matrix for which an intermediate result has already been calculated. As the calculation of each cell requires the intermediate result of its left, upper and left-upper neighbor as input, the horizon also provides the input data for all cells ready for calculation in a next calculation step. The horizon comprises a sequence of neighboring cells of the matrix Az for which the following conditions hold true (assuming the left-most and upper-most cell of the matrix has the lowest row and column index). The intermediate result for said horizon cells and for all cells in the matrix having a lower or equal row index value and/or having a lower or equal column index value have already been calculated. At least the cell having a higher row index and having a higher column index has not yet been calculated (if Az(i,j) is a horizon cell, then at least Az(i+1,j+1) has not been calculated yet, but all cells having a row index ≤i or have a column index ≤j have already been calculated).

According to the embodiment depicted in FIG. 3, the cells are divided into cell groups. To explain the depicted embodiment by way of an example, it will be assumed that cell groups (3,0), (2,2) and (1,4) may have been executed. Thereby, all their respective output cells were marked as useless as any alignment passing through any of said cell groups (3,0), (2,2) and (1,4) would return a less optimal result than the current oab-threshold. Upon starting the execution of any of the cell groups (2,3) and (3,1), it may have been determined that the calculation of said cell groups can in no case return an alignment score being more optimal than the current oab-threshold, because all the input cells provided by the cell groups (3,0), (2,2) and (1,4) are marked as useless. Thus, instead of calculating the intermediate results for the cells in the starting cell groups (2,3) and (3,1), all cells in said starting cell groups are marked as useless. The calculation of intermediate results and/or the propagation of the label 'useless' may have proceed until the moment in time as depicted in FIG. 3: the cell groups 312, 311 and the other two cell groups indicated with hatching are cell groups which are ready for execution at the depicted moment in time. Upon starting execution, at least cell group 311 (group (3,2)) will abort its execution, because all cells providing input to it have been marked as useless.

The left-most, uppermost "start" cell group is considered as ready per default. The even distribution in cells to the cell groups is advantageous as said feature allows to easily keep track of the readiness (ability to provide calculated intermediate results or information that all the group's cells were marked as 'useless' as input to other cell groups) of the individual cell groups, as all dependencies between the groups are clear. At the beginning of the execution of each cell group it is checked if all cells providing input to the cell group starting execution are marked as useless or not.

Figure 4A:
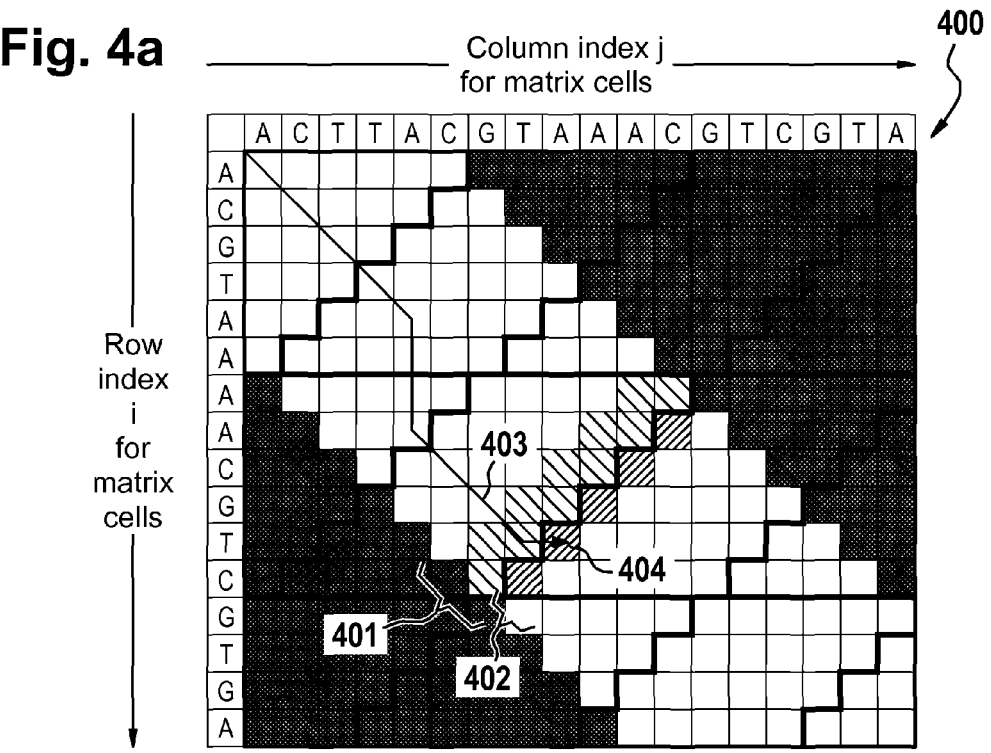
FIGS. 4a and 4b shows the matrix of intermediate results at two moments during the calculation of an alignment in accordance with an exemplary embodiment.
Figure 4B:
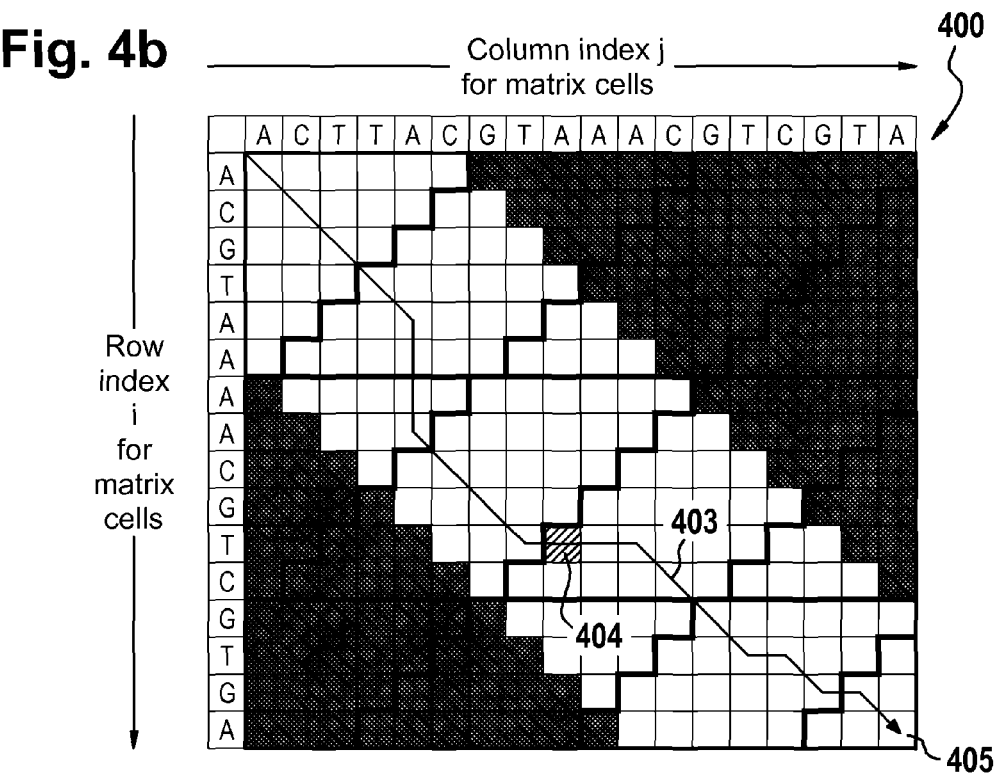

FIGS. 4a and 4b show the matrix of intermediate results at two different moments during the calculation of an alignment between two DNA sequences sz (corresponding to row index i) and t (corresponding to column index j). The matrix of cells comprises a plurality of triangle shaped and diamond shaped cell groups, each diamond shaped cell group being S cells in width and having S cells at each diagonal cell group border. In the depicted embodiment, S=6. The parameter K is selected as S−1=5 and is used to specify a sub-set of cells fulfilling the equation |i−j|≤K. Said sub-set is depicted in FIG. 4a as cells having a white background. Cells not fulfilling said equation are illustrated by a dark hachuring of the cell background. FIG. 4a depicts a moment during the calculation of the final alignment score scz at which the alignment has already been calculated up to the cell 404 (it is an 'intermediate alignment'). The first sub-alignment starting from the left upper corner cell and terminating at cell 404 is indicated by the arrow 403. In order to calculate the prospective final alignment score PZ (404) for the cell 404, the intermediate result Fz (404) is calculated by taking as input the intermediate results provided by the three cells being the left-, upper-, and left-upper neighbor cell of cell 404. In addition, an optimum alignment score value scsub is calculated for the yet un-aligned sub-strings of sz and t: scsub=MATCHES*BEST_MATCH+ GAPPENALTY (gaps). The highest number of matches theoretically possible is limited by the number of un-aligned characters of the shorter one of the two yet un-aligned sub-strings of the two strings. At cell 404, i=10 and j=8, sz having length N=16, t having length M=18. Thus, MATCHES=min(M−(j+1), N−(i+1))=min(18−8+1, 16−(10+1))=min(9, 5)=5. The BEST_MATCH parameter value may be a constant representing the highest score obtainable for a matching character pair. By multiplying the MATCHES with the BEST_MATCH value, an intermediate optimum possible alignment score scsub can be obtained very quickly for the non-aligned characters at cell 404. This value also depends on the number of gaps to be expected for the un-aligned characters. In this example, the minimum number of gaps to be expected is three. The number of gaps which need to be introduced can be calculated by determining a first number m=9 of still un-aligned characters of string t at 404, determining a second number n=5 of still un-aligned characters of string sz at cell 404, and calculating a number |m−n|−1=4−1=3 of characters which cannot be aligned to each other for any alignment covering cell 404, this being the minimum number of gaps to be introduced for aligning the not-yet aligned characters oft and sz.

All 5 cells 402 may be calculated in parallel by different units of one stream multiprocessor of a GPU, respectively taking their input values from three cells of the set of 11 cells 401. Cells 402 are a set of cells ready for execution. The input required by cells 402 is provided by the cells 401.

FIG. 4b shows the matrix Az at the moment when the final alignment score has finished calculation. The calculated alignment 403 covers the left upper starting cell and terminates at cell 405. The intermediate result Fz (405) is used as the final alignment score scz for strings sz and t.

Figure 5:
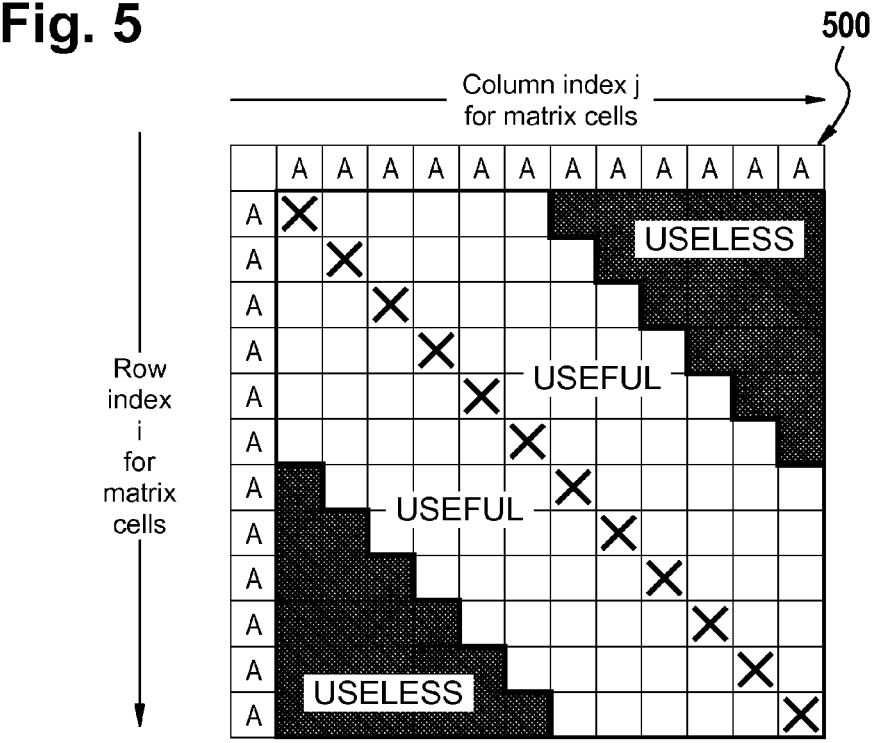
FIG. 5 shows an alignment of two identical DNA sequences within the boundary of K in accordance with an exemplary embodiment.
Figure 6:
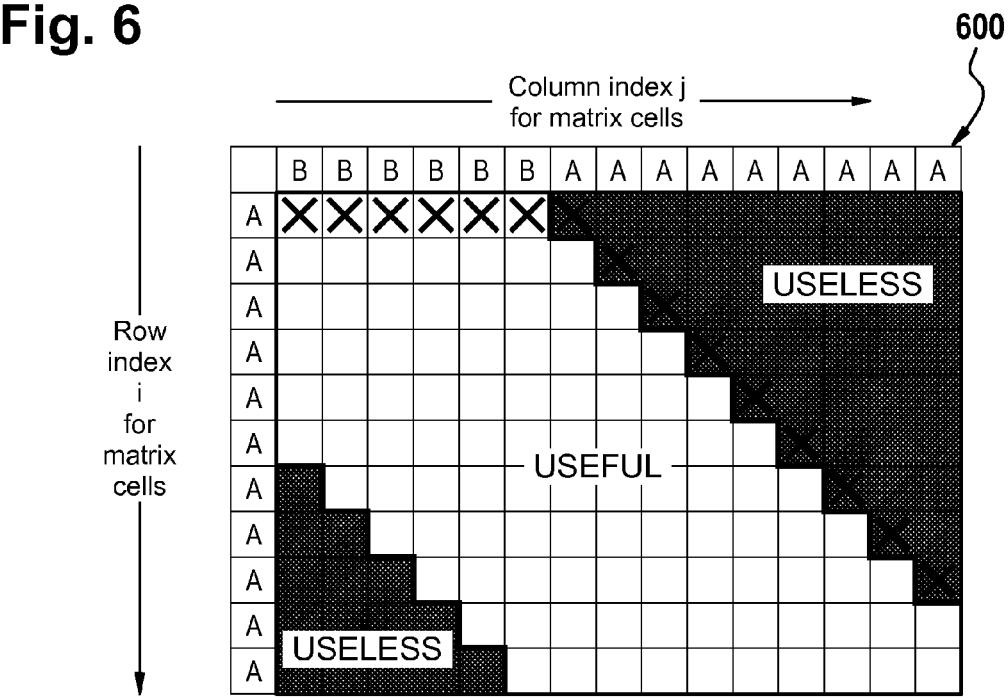
FIG. 6 shows an alignment of two sequences, the alignment lying partially outside the boundary of K in accordance with an exemplary embodiment.

FIGS. 5 and 6 show the matrix for K=5, wherein the alignment of two strings sz, t for calculating the initial oab-threshold is marked with the symbol X and wherein cells marked as useless in dependence on K are also depicted. FIG. 5 shows an alignment where the two aligned sequences are identical. The oab-threshold derived from a matrix according to FIG. 5 will be exactly equal to scz and will never need to be updated. FIG. 6 illustrates the situation that the final alignment lies outside the sub-set of cells specified by K as 'useful'. This can happen if the two aligned strings are less similar than expected/than covered by the chosen K. In this situation, the oab-threshold will be updated by a more accurate value during the calculation of the final alignment scores of one or more of the strings, because the initial step won't return the oab-threshold=scz.

It is an object of the invention to provide for an improved computer implemented method, computer program product and computer system for quickly and accurately finding a sequence from a set of sequences being the best matching sequence in respect to a reference sequence. This object is solved by the features of the independent claims. Preferred embodiments of the invention are given in the dependent claims. If not explicitly stated otherwise, e.g. by making explicit reference only to particular embodiments, embodiments of the invention can be combined freely with each other.

A graphics processing unit (GPU) refers to a processing unit which is specialized for compute-intensive, highly parallel computation; this is exactly what graphics rendering and several other highly parallelizable computation tasks are about. According to embodiments, a 'GPU' is a multiprocessor computing device capable of executing a plurality of threads in parallel. The computing device may act as a coprocessor to the main CPU, thereby allowing off-loading data-parallel, compute-intensive portions of applications running on the main CPU onto the GPU. Preferentially, a processing unit of the GPU is a stream multiprocessor. A GPU may have several memory units of different functions, whereby some of these memory units are used as a 'shared memory', herein also referred to as 'local memory', as said memory is accessible (shared') by a group of threads running on the GPU. A 'thread' as used herein is a thread of execution in a program function. A 'group of threads' or 'thread block' as used herein is a batch of threads that can cooperate together by effectively sharing data through some shared memory, preferentially a fast memory, and that can synchronize their execution to coordinate memory access. In addition, a GPU may comprise one or more central memories accessible (but typically with slower performance compared to accessing the shared memory) by each of the stream multiprocessors.

A 'string' as used herein is any sequence of symbols, in particular strings representing natural language text, DNA, RNA or protein sequences. A symbol may be a character, a special character, a number or the like.

An 'alignment score' as used herein is a similarity measure being indicative of the similarity of two aligned strings. The alignment may be based, for example, on a Needleman-Wunsch algorithm, with affine gap penalty and possibly different costs for different pairs of matching/mismatching characters.

In one aspect, the invention relates to a computer-implemented method for finding a best matching string sopt among a set Z of strings for a reference string t. Z may comprise one or more strings. The method comprises representing, for each pair of strings sz and t, a dynamic programming problem (i.e. the problem of calculating a final alignment score scz for the strings sz and t) as a matrix Az of cells. Each cell Az(i,j) represents an intermediate result Fz(i,j) to be calculated, wherein Fz(i,j) is an intermediate result for the final alignment score and is calculated as: Fz(i,j)=G(Fz(i−1, j−1), Fz(i, j−1), Fz(i−1,j), cz(i,j)). Thereby, each character of the string sz is represented by a row of said matrix Az, and each character of the string t is represented by a column of said matrix Az. String sz may be of length N, string t may be of length M, i being a row index and j being a column index of the matrix Az. The indices i and j respectively are larger than or equal to 0. G is an optimization function and cz is a cost function. The cost function may depend, for example, on the type of characters to be aligned at a particular cell.

In exemplary embodiments, a method for finding a best matching string among a set of strings includes calculating a current optimal alignment boundary threshold, referred herein as 'oab-threshold'. The threshold may be calculated at least one time for calculating an initial oab-threshold value. For each string sz of the set Z of strings, a prospective final alignment score Pz(i,j) of a candidate alignment of the strings sz and t for a cell Az(i,j) are calculated. The prospective final alignment score Pz(i,j) being calculated as Pz(i,j)=Fz(i,j)+scsub, wherein scsub is the optimum alignment score value that can possibly be calculated for a sub-alignment of the strings sz and t starting anyone of the cells Az(i+1,j), Az(i,j+1) or Az(i+1,j+1) and terminating at a cell Az(N−1,M−1). For each string sz of the set Z of strings, it is determined if the prospective final alignment score Pz(i,j) calculated for the cell Az(i,j) improves the current oab-threshold and if no improvement is determined, the calculation of the candidate alignment terminates at said cell Az(i,j) and prohibis any extension of the candidate alignment covering said cell Az(i,j). A cell for which no improvement is determined may be marked as 'useless'. In effect, the calculation of an intermediate result is prohibited for any cell of the matrix if all alignments comprising said cell contain at least one useless cell. An extension of an alignment may be based on increasing at least once the row and/or column index by 1 for calculating a new intermediate result for extending the current intermediate alignment. On the other hand, if an improvement is determined, the calculation of the candidate alignment for calculating the final alignment score scz for said string sz continues.

Depending on whether the optimizing function is a minimizing or a maximizing function, the meaning of some parameters differ. In case the optimization function is a maximizing function, the oab-threshold specifies a threshold score that a prospective final alignment score Pz(i,j) of any candidate alignment of sz and t covering cell Az(i,j) must exceed for not ruling out said candidate alignment as a candidate for an optimum alignment (i.e., an alignment of the best matching string sopt with t). The value scsub is a maximum possible alignment score value for said sub-alignment. The improvement of the current oab-threshold is determined if the calculated prospective final alignment score Pz(i,j) for the cell Az(i,j) is above the current oab-threshold. In the case the optimization function is a minimizing function, the oab-threshold specifies a threshold score that a prospective final alignment score Pz(i,j) of any candidate alignment of sz and t covering cell Az(i,j) must be smaller than for not ruling out said candidate alignment as a candidate for an optimum alignment of the best matching string $s_{opt}$. The value $sc_{sub}$ is a minimum possible alignment score value for said sub-alignment and the improvement of the current oab-threshold is determined if the calculated prospective final alignment score Pz(i,j) for the cell Az(i,j) is below said current oab-threshold.

In exemplary embodiments, Fz(i,j) is calculated exactly in accordance with the dynamic programming problem. To the contrary, $sc_{sub}$ is an estimate value that can be calculated comparatively quickly. Thus, Pz(i,j) is a combination of an exactly calculated value for a first sub-alignment terminating at cell Az(i,j) and a prospective optimal alignment score value for a second sub-alignment of the currently un-aligned characters of sz an t. Given a current pair of strings (sz, t), a plurality of possibilities for aligning said strings exists. A candidate alignment is one of said possible alignment variants being currently calculated, whereby the optimum sub-alignment has already been calculated until cell Az(i,j), while all string symbols having a higher row- or column index than said cell are still un-aligned. After having calculated a final alignment score for each of the strings in Z (or at least a prospective alignment score in case the alignment never continued till the end of a string sz), the optimum (minimum/maximum) alignment score is determined. The 'best matching string' $s_{opt}$ in respect to string t is any string sz of the set of strings Z reaching the highest (or the lowest) final alignment score with string t for G being a maximizing function (for a minimizing function) of all the strings of Z.

It may be possible to determine in advance (by determining if an improvement is obtained or not) that the optimal alignment "coming through" or "using" that particular cell Az(i,j) would result in a final alignment score being less optimal than the current oab-threshold, regardless of what characters to the sequences sz and t contain later (later in respect to the row and column indices of the cell Az(i,j)). In such a case, the calculation of the alignment of the sequences sz and t covering said cell Az(i,j) is aborted, thereby saving time and processing power. Aborting the calculation of an alignment at a particular cell Az(i,j) implies that the intermediate alignment and corresponding intermediate alignment score Fz(i,j) having already been calculated are kept and may be used e.g. as input for some other alignments sharing some of the aborted alignment's already calculated cells. However, no further cell is selected for extending the intermediate alignment covering said 'useless' cell Az(i,j). In effect, the calculation of an intermediate result is prohibited for any cell if all alignments comprising this cell contain at least one useless cell. The expressions 'intermediate result' of a cell Az(i,j), the expression Fz(i,j) representing an exact calculation of the alignment score of an alignment terminating at said cell are used herein as synonyms. According to embodiments, the value for the currently evaluated cell can be "discarded" for aborting the calculation of the alignment by setting its intermediate result to infinity (for minimizing functions) or minus infinity (for maximizing functions). In addition or alternatively, said cell may be flagged as "useless".

In exemplary embodiments, features of the present invention may be advantageous, because according to state-of-the-art implementations used for solving dynamic programming problems the complexity of finding the optimal alignment of two compared sequences and the corresponding optimal alignment score is quadratic. Embodiments of the invention allow to significantly reduce the processing time required for calculating the optimal alignment (i.e., determining one out of one or more strings of Z being the most similar one to a search string t). Thus, embodiments of the invention allow a quick determination of the best matching string sz out of a set Z of strings in respect to a reference sequence t. Typically, the strings sz are stored into a database which may comprise several hundred million strings, each string comprising more than several hundred million characters.

According to some embodiments, the function G and the cost function may be specified according to the Needleman-Wunsch algorithm, the Smith-Waterman algorithm or any other dynamic programming algorithm used in the art for aligning sequences to each other. According to some embodiments employing a Needleman-Wunsch algorithm with linear gap penalty as the dynamic programming problem G, the following equations apply:

$$c(i,j) = \begin{bmatrix} +1 & \text{if } s[i] = t[j] \\ -1 & \text{otherwise} \end{bmatrix},$$

and G(F(i−1,j−1), F(i, j−1), F(i−1,j),c(i,j))=max(F(i−1,j−1)+PP, F(i,j−1)+GP, F(i−1,j)+GP) wherein PP=c(i,j) and wherein PP is a predefined penalty function and GP is a predefined gap penalty value. Preferentially, GP is −10.

According to exemplary embodiments, it has been observed that the performance gain is particularly apparent for the comparison of strings having a high degree of similarity. According to embodiments, the sequences sz of the set Z of sequences and the search sting t having been aligned to each other show a sequence identity of >60%, more preferentially >80%, and even more preferentially >90% sequence identity. For example, DNA fragments of different humans representing the same gene and having been aligned to each other often show a fraction of identical characters of >95%. While the similarity between two aligned characters may be calculated based on a complex scoring function taking into consideration also the context of the aligned characters in their respective sequences, a sequence identity of 95% simply implies that there exists at least one alignment of said two strings according to which more than 95% of the symbols of the shorter one of the two strings could be aligned to a respectively identical symbol of the other string.

According to embodiments, the optimum alignment score value $sc_{sub}$ for the cell Az(i,j) is calculated as scsub=MATCHES*BEST_MATCH+GAPPENALTY (gaps). Thereby, the MATCHES parameter value is the maximum possible number of matching character pairs in the second sub-alignment (comprising the characters not yet aligned in the first sub-alignment). It may be calculated as MATCHES=min(M−(j+1), N−(i+1)). The BEST_MATCH parameter is the highest score obtainable for any possible combination of two aligned characters (for maximizing functions) or is the smallest score obtainable (for minimizing functions). The gaps parameter is a minimal possible number of gaps occurring in the sub-alignment. The gaps parameter may be calculated as gaps=max (0, |M−(j+1)−(N−(i+1))|−1). The GAPPENALTY(gaps) function is a monotone function which for a given number of gaps that is >0 returns a penalty cost, the penalty cost being a negative value for maximizing functions and being a positive value for minimizing functions.

For example, when amino acids are compared, the BEST MATCH score may be given for any pair of identical amino acids being aligned together. In case two aligned amino acids have similar chemical properties such as, for example, being both hydrophobic, a matching score between the BEST MATCH score and zero may be given. In case two characters/amino acids cannot be aligned at all, a matching score of zero may be given. Depending on the embodiment, the GAPPENALTY(gaps) may in addition depend on the number of gap opening events, wherein gap opening events are represented by a gap opening penalty and gap extensions are represented by a gap extension penalty. According to preferred embodiments, GAPPENALTY(gaps)=gap_open+gap_extend*gaps, wherein gaps is the number of gaps introduced into the second sub-alignment, the gap_open parameter value represents a penalty value for introducing a new gap into said sub-alignment and wherein the gap_extend value represents a penalty value for extending an already existing gap or sequence of gaps by one element. Typically, the penalty for extending a gap is lower than for introducing a new gap (a principle also referred to as 'affine gap penalty'). A linear gap penalty is introduced in case gap_open=0.

Assuming that string sz is of length N, string t is of length M, then the number n of characters of sz which are not-yet-aligned in a current intermediate alignment terminating at cell A(i,j) is |N−i−1|. The number m of characters of t which are not-yet-aligned in said current intermediate alignment is |M−j−1|. By selecting the minimum of (m,n), the maximum possible number of not-yet-aligned characters of said intermediate alignment which may successfully be aligned upon having calculated the final alignment is determined. For example, in case a final alignment score scz for a string sz is calculated, the optimization being a minimization, then it may be determined that scz<oab-threshold. In this case, scz is used as the new oab-threshold and the calculation of the final alignment score for another sz+1 is started. Said steps may be repeated until for all strings in Z a final alignment score scz is calculated or the calculation of a respective final score was aborted.

According to embodiments, all strings of Z are sorted according to their difference in length in respect to the length of the string t. The calculation of the final alignment score may then be executed for all the strings sz in the order of a growing length difference. This may be advantageous as it ensures that during the calculation of the final alignment score for the first one(s) of the strings an already highly accurate oab-threshold (i.e., an oab-threshold being close to the optimum alignment score $sc_{opt}$) is calculated. This allows to mark a larger number of cells as useless in succeeding string alignments, thereby saving processing time. According to embodiments, in the case of length equality of two or more strings sz in respect to t, the string to start with may be selected randomly from said two or more strings.

According to embodiments comprising a hardware environment being operable to execute the calculation of a number R alignments in parallel, R being an integer larger than 1, the calculation of the final alignment score may be executed for R out of the Z strings in parallel, wherein said R strings are selected from the set of strings in the order of their growing length difference.

According to embodiments, calculating an initial current oab-threshold includes determining an integer K, selecting a string from the set of strings, e.g. a string having the same or a similar length as t. For the selected string, determining a sub-set of cells of the matrix, said sub-set comprising all cells of the matrix Az having a row index i and a column index j fulfilling the equation |i−j|≤K, calculating an approximate final alignment score AFz(N−1,M−1) for the selected string sz by applying the dynamic programming problem on the matrix Az until the cell Az(N−1,M−1) is reached, thereby selectively taking as input to the dynamic programming problem only the intermediate results of those cells of the matrix Az which belong to the determined sub-set and using the calculated approximate final alignment score as the current oab-threshold.

Said features are advantageous, because the initial oab-threshold is calculated highly accurately at least for strings sz and t being highly similar to each other. In this case it can be assumed that similar strings will return a final alignment somewhere around the matrix diagonal. If the strings are highly similar to each other, cells lying far away from the diagonal of the matrix can be considered as almost "a priori" useless. By omitting the calculation of intermediate results for cells whose row and column indices do not fulfill the equation |i−j|≤K, the calculation of the initial oab-threshold can be accelerated while still getting accurate initial threshold values in the vast majority of cases. The smaller K, the higher the number of cells considered as useless. According to embodiments, in case K was chosen too small, this will not result in a sub-optimal final alignment score. In case K was chosen too large, a more appropriate oab-threshold will be dynamically obtained during execution of the alignments.

On the other hand, a K chosen too large may prolong the time for calculating an alignment as more cells have to be computed for determining the initial oab-threshold value in case less cells are marked as 'useless' a priori.

Updating a current oab-threshold by a more accurate value may take additional time, but this time investment is typically overcompensated, because the possible search space for each sequence alignment is decreased by updating the oab-threshold, thereby further speeding up the string alignment process for succeeding alignments. Thus, said features may be advantageous, because the final alignment score calculated for each of the sequences is approximated throughout the whole best-match search by updating the current oab-threshold.

According to embodiments, for calculating the initial oab-threshold, all strings of Z are sorted according to their difference in length in respect to the length of the string t. Then, one of the one or more strings having the smallest length difference in respect to t are used as the selected string for calculating the initial oab-threshold. Again, in case of length equality of two or more of said sequences, one of them may be selected randomly. According to further embodiments, initially calculating the current oab-threshold comprises initializing the oab-threshold as negative infinity in case the optimization function is a maximizing function and as positive infinity in case the optimizing function is a minimizing function.

According to embodiments, the calculation of the final alignment score scz of each of the strings sz includes dividing the cells of the matrix Az into groups of cells, at least some of the cell groups respectively taking intermediate results of cells of one or more other cell groups as input. Upon having calculated intermediate results for all cells of any one of the cell groups, marking these cells of said cell group as useless, for which the prospective final alignment score $Pz(i,j)$ does not improve the current oab-threshold. Upon starting the calculation of any one of the cell groups, checking if all cells providing input to said one cell group are marked as useless cells and aborting the calculation of any one of the cell groups in case the checking returned as result that all the cells providing input to said cell group are marked as useless. In this case, all cells within said cell group or at least the cells of said cell group providing input to cells of other cell groups are also marked as useless.

Said features may be advantageous for the following reason: at the end of the computation of each group of cells, it is determined if all the cells in said cell group's lower border row have been marked as useless. If so, this information is passed on to said cell group's lower adjacent neighboring cell group. The method may further comprise a setp of determining if all the cells in said cell group's right border (two cells in each row that have the highest column indices) have been marked as useless. If so, this information is passed on to said cell group's right adjacent neighboring cell group. This passing-on may be implemented in some embodiments such that any cell group starting execution checks whether all of the cells of adjacent cell groups providing input to said starting cells have been marked as useless. If so, this information is propagated by also marking all cells of the starting cell as useless. Propagating the uselessness of the cells of a cell group providing the input for another cell group is advantageous, because this information allows said other cell group having just started execution to determine if the execution of said cell group has a chance of contributing to a final alignment potentially having the optimum alignment score.

Each cell group starting execution, i.e., starting to calculate the intermediate results of all cells within said cell group, may determine if the intermediate results of the upper and left neighboring cell groups have all been marked as useless. If so, the starting of the execution of said cell group is aborted, because this finding implies that the intermediate alignment score having been obtained so far for the cells of the adjacent cell groups providing the input for the starting cell group is so low (for a maximizing function) that there does not exist any chance—even in case all not—yet aligned characters would from now on always yield the BEST MATCH value, that there does not exist a chance of obtaining a higher alignment score value than the current oab-threshold value.

If it was determined that in the upper and the left neighboring cell groups all the cells have been marked as useless, the calculation of the cell group starting its execution can be omitted, because any alignment path leading to any cell inside said cell group starting execution must go either through said cell groups left adjacent cell group or through its upper adjacent cell group.

According to other embodiments, the step of checking for uselessness is executed only for the cells actually providing input to said starting cell group, thereby further speeding up the calculation. According to some embodiments, each of the cell groups (except for some cell groups at the borders of the matrix) comprises 1300×1300 cells due to CUDA architectural limitations. Typically, each of the strings is a couple of millions of characters long. Thus, the number of useless cells that are actually unnecessarily computed within each currently executed cell group is only a small fraction of the whole matrix. According to embodiments, the parameter K is chosen in dependence on the hardware architecture used for solving the dynamic programming problem. It is the largest number for which all the GPU's stream multiprocessors can be utilized without losing performance when compared to smaller Ks.

For example, K may be chosen to be about 10000. The smaller K, the less cells need to be computed, but the less accurate the initial oab-threshold is. The greater K, the longer the time for calculating the initial oab-threshold, but the better approximation of the score scz is returned as the initial oab-threshold.

According to some embodiments, the matrix is initialized by setting the value of all cells $Az(i,j)$ not fulfilling the equation $|i-j| \leq K$ to $-\infty$ for maximizing functions and to $\infty$ for minimizing functions. Instead of setting said value to + or − infinity, the corresponding cell may likewise be marked as 'useless'. This step drastically reduces the calculation time because it is not necessary anymore to calculate the whole matrix.

According to embodiments, the division into groups of cells includes specifying a constant S; dividing all cells of the matrix Az into a grid $g(y, x)$ of non-overlapping, adjacent cell groups, wherein each cell group $g(y,x)$ comprises a left upper starting cell $Az(i,j)$. Each cell group is specifiable by selecting the starting cell $Az(i,j)$ of the matrix as starting cell of said cell group, selecting all cells of row i lying within the matrix and having a column index j within the range $[j-a+0, j-a+1, \ldots, j-a+(S-1)]$ to get S cells, wherein $a=0$ and repeating step b), wherein in each repeat the row index i is incremented by 1 and wherein a is incremented by 1, said repeat being executed until a is equal to S−1, thereby selecting S cells in each of S rows for said cell group altogether. The starting cell of one of the cell groups has row index i=0 and column index j=0, and wherein each of the matrix cells belongs to exactly one cell group of the grid of cell groups.

According to embodiments, a number of processing units are provided for parallel execution of multiple cell groups of the matrix. Each of the processing units has assigned a local memory. The method comprises determining a local memory size, the local memory size being the minimum size of any of the local memories; dividing the local memory size by 3*cell memory size for obtaining a division result, wherein the cell memory size is the storage space required for storing one of the intermediate results $Fz(i,j)$; obtaining the value S by rounding the division result down to the nearest whole value; determining a number h by dividing the number of processing units by 2 and reducing the division result by 1; and finally specifying K as $K=(h*S)-1$. For example, the parameter h may be calculated for a graphic card comprising 14 GPU stream processors as h=(the number of processing units/2)−1=14/2−1=6. $K=6*S\times 1$.

The proposed determination of S and/or K may be advantageous as the proposed determination yields the best tradeoff between performance of a first step for calculating the initial oab-threshold value and the accuracy of the initially calculated oab-threshold in dependence on the hardware environment used for solving the dynamic programming problem, thus making optimum usage of the available hardware.

According to embodiments, each cell group having finished execution provides the intermediate results calculated for the cells of its lowermost cell row to a lower, adjacent cell group (if any) as input. In addition, it provides the intermediate results calculated for the two rightmost cells of each of its rows to a right adjacent cell group (if any) as input. The provision may be implemented in the form of storing the intermediate results in a result container data structure. The result container data structure may be any data structure, e.g. an array, being accessible by another processing unit starting the execution of the cell group to receive the intermediate results.

Each cell group starting execution receives the intermediate results calculated for the cells of the lowest row of its upper adjacent cell group (if any) as input. In addition, said cell group starting execution receives the intermediate results calculated for the two rightmost cells of each of its left-adjacent cell group (if any) as input. For example, a cell group starting execution may be adjacent to a first cell group and to a second cell group, wherein the first cell group is an upper adjacent cell group and the second cell group is a left adjacent cell group. The cells providing input to the cell group starting execution consist of all cells of the lower most row of the first cell group and the two cells in each row of the second cell group having the highest column index in their respective row. Said features are advantageous as the number of cell groups comprising cells providing input for another cell group is very small. As a consequence, the interdependency of cell groups is reduced and a parallel execution of the cell groups is possible for a plurality of different cell groups. Only said cells provide input to the cell groups starting execution and need to be checked for usefulness.

According to embodiments, each of the cell groups is assigned to one of a plurality of processing units; this step may be executed, for example, by a CPU of a standard computer system. Then, each of the processing units having assigned one of the cell groups execute their respective cell groups in parallel, thereby filling each cell of said cell group with a calculated intermediate result. Thereby, the execution of the plurality of cell groups is coordinated in a way ensuring that the execution of any of the cell groups is started only in case an execution of an adjacent left cell group and an adjacent upper cell group is already finished. In case a cell group lies at a border of the matrix, it may receive at least a part of its input per default and a checking for the neighbor cell group to have finished execution is not required.

According to embodiments, starting a cell group comprises the step of determining if all cells providing input to said cell group starting execution were marked as useless. If this is the case, all cells of the cell group starting execution are marked as useless and the execution of said cell group having started execution is aborted. According to other embodiments, at least those cells of the cell group starting execution are marked as useless which provide its intermediate result as input to another cell group. The execution of said cell group having started execution is likewise aborted in these embodiments.

Upon having calculated a result of the execution of any of the cell groups, said result is stored to a result container data structure, said data structure being stored in a memory, preferentially in a central memory. The central memory is accessible by any of the processing units executing the cell groups in parallel. It is also accessible by a further processing unit, typically a CPU, being responsible for distributing the cell groups among the plurality of processing units operating in parallel. Then, the results of each of the cell groups are returned, e.g. by storing them into the result container data structure, thereby providing the final alignment score scz for the sequences sz and t as a result of the dynamic programming problem.

According to embodiments, the above method steps are encoded in the form of a high-level programming language such as, for example, Java, C, C#, C++ or the like. This may ease the specification and modification of the dynamic programming problem and its integration into existing applications.

As will be appreciated by one skilled in the art, one or more aspects of the present invention may be embodied as a system, method or computer program product. Accordingly, one or more aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, one or more aspects of the present invention may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Program code, when created and stored on a tangible medium (including but not limited to electronic memory modules (RAM), flash memory, Compact Discs (CDs), DVDs, Magnetic Tape and the like is often referred to as a "computer program product". The computer program product medium is typically readable by a processing circuit preferably in a computer system for execution by the processing circuit. Such program code may be created using a compiler or assembler for example, to assemble instructions, that, when executed perform aspects of the invention.

The terminology used herein is for the purpose of describing particular embodiments only and is not intended to be limiting of embodiments. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of embodiments have been presented for purposes of illustration and description, but is not intended to be exhaustive or limited to the embodiments in the form disclosed. Many modifications and variations will be apparent to those of ordinary skill in the art without departing from the scope and spirit of the embodiments. The embodiments were chosen and described in order to best explain the principles and the practical application, and to enable others of ordinary skill in the art to understand the embodiments with various modifications as are suited to the particular use contemplated.

Computer program code for carrying out operations for aspects of the embodiments may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of embodiments are described above with reference to flowchart illustrations and/or schematic diagrams of methods, apparatus (systems) and computer program products according to embodiments. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The invention claimed is:

1. A computer-implemented method for finding a best matching string among a set of strings for a reference string, the method comprising:

representing, for each of the set of strings paired with the reference string, a dynamic programming problem for calculating a final alignment score as a matrix of cells, each cell representing an intermediate result to be calculated;

calculating a current optimal alignment boundary threshold, for each string of the set of strings, executing:

calculating a prospective final alignment score of a candidate alignment of the each of the set of strings and the reference string for each cell;

based on determining, that prospective final alignment score improves the current optimal alignment boundary threshold, calculating a final alignment score for the string of the set of strings associated with the cell; and based on determining, that prospective final alignment score does not improve the current optimal alignment boundary threshold, aborting the calculation of a candidate alignment covering the string of the set of strings associated with the cell, wherein the optimum alignment score value for each of the cells is calculated as MATCHES*BEST_MATCH+GAPPENALTY(gaps), wherein MATCHES=min(M−(j+1), N−(i+1)), wherein the MATCHES parameter value is the maximum possible number of matching character pairs in the sub-alignment, BEST_MATCH is the highest score obtainable for any aligned character pair for maximizing functions or the smallest obtainable score for minimizing functions, gaps is a minimum possible number of gaps occurring in the sub-alignment; and GAPPENALTY(gaps) is a monotone function which for a given number of gaps that is greater than zero that returns a penalty cost, the penalty cost being a negative value for maximizing functions and being a positive value for minimizing functions.

2. The computer-implemented method of claim 1, further comprising:
sorting all strings of the set of strings according to a difference in length with respect to a length of the reference string,
wherein the calculation of the final alignment score is executed for all strings of the set of strings in the order of a growing length difference.

3. The computer-implemented method of claim 1, wherein initially calculating the current optimal alignment boundary threshold comprises:
determining an integer K;
selecting a string from the set of strings, and for the selected string, executing:
determining a sub-set of cells of the matrix, said sub-set comprising all cells of the matrix having a row index i and a column index j fulfilling the equation $|i-j|\leq K$; and
calculating an approximate final alignment score for the selected string by applying the dynamic programming problem on the matrix until the cell having an index of (N−1, M−1) is reached, thereby selectively taking as input to the dynamic programming problem only the intermediate results of those cells of the matrix which belong to the sub-set of cells; and
using the calculated approximate final alignment score as the current optimal alignment boundary threshold.

4. The computer-implemented method of claim 1, further comprising:
sorting all strings of according to their difference in length with in respect to the length of the reference string; and
using one of the one or more strings having the smallest length difference as the selected string for calculating the initial optimal alignment boundary threshold.

5. The computer-implemented method of claim 1, wherein initially calculating the current optimal alignment boundary threshold comprises initializing the optimal alignment boundary threshold as negative infinity for a maximizing optimization function and as positive infinity for a minimizing optimizing function.

6. The computer-implemented method of claim 1, wherein the calculation of the final alignment score of each of the set of strings comprises:
dividing the cells of the matrix into groups of cells, at least some of the cell groups respectively taking intermediate results of cells of one or more other cell groups as input;
upon having calculated intermediate results for all cells of any one of the cell groups, marking these cells of said cell group as useless, for which the prospective final alignment score does not improve the current optimal alignment boundary threshold;
upon starting the calculation of any one of the cell groups, checking if all cells providing input to said one cell group are marked as useless cells; and
aborting the calculation of any one of the cell groups in case the checking returned as result that all the cells providing input to said cell group are marked as useless and marking at least those cells in the cell group aborting its execution as useless, which are operable to provide input to another cell group.

7. A computer program product for finding a best matching string among a set of strings for a reference string, the computer program product comprising:
a computer readable storage medium having computer readable program code embodied therewith, the computer readable program code configured to execute a method comprising:
representing, for each of the set of strings paired with the reference string, a dynamic programming problem for calculating a final alignment score as a matrix of cells, each cell representing an intermediate result to be calculated;
calculating a current optimal alignment boundary threshold,
for each string of the set of strings, executing:
calculating a prospective final alignment score of a candidate alignment of the each of the set of strings and the reference string for each cell;
based on determining, that prospective final alignment score improves the current optimal alignment boundary threshold, calculating a final alignment score for the string of the set of strings associated with the cell; and
based on determining, that prospective final alignment score does not improve the current optimal alignment boundary threshold, aborting the calculation of a candidate alignment covering the string of the set of strings associated with the cell, wherein the optimum alignment score value for each of the cells is calculated as MATCHES * BEST_MATCH +GAPPENALTY(gaps),
wherein MATCHES=min(M-(j+1), N-(i+1)), wherein the MATCHES parameter value is the maximum possible number of matching character pairs in the sub-alignment, BEST_MATCH is the highest score obtainable for any aligned character pair for maximizing functions or the smallest obtainable score for minimizing functions, gaps is a minimum possible number of gaps occurring in the sub-alignment and GAPPENALTY(gaps) is a monotone function which for a given number of gaps that is greater than zero that returns a penalty cost, the penalty cost being a negative value for maximizing functions and being a positive value for minimizing functions.

8. The computer program product of claim 7, further comprising:
sorting all strings of the set of strings according to a difference in length with respect to a length of the reference string,
wherein the calculation of the final alignment score is executed for all strings of the set of strings in the order of a growing length difference.

9. The computer program product of claim 7, wherein initially calculating the current optimal alignment boundary threshold comprises:
determining an integer K;
selecting a string from the set of strings, and for the selected string, executing:
determining a sub-set of cells of the matrix, said sub-set comprising all cells of the matrix having a row index i and a column index j fulfilling the equation $|i-j|\leq K$; and
calculating an approximate final alignment score for the selected string by applying the dynamic programming problem on the matrix until the cell having an index of (N−1, M−1) is reached, thereby selectively taking as input to the dynamic programming problem only the intermediate results of those cells of the matrix which belong to the sub-set of cells; and using the calculated approximate final alignment score as the current optimal alignment boundary threshold.

10. The computer program product of claim 7, further comprising:

sorting all strings of according to their difference in length with in respect to the length of the reference string; and using one of the one or more strings having the smallest length difference as the selected string for calculating the initial optimal alignment boundary threshold.

11. The computer program product of claim 7, wherein initially calculating the current optimal alignment boundary threshold comprises initializing the optimal alignment boundary threshold as negative infinity for a maximizing optimization function and as positive infinity for a minimizing optimizing function.

12. The computer program product of claim 7, wherein the calculation of the final alignment score of each of the set of strings comprises:

dividing the cells of the matrix into groups of cells, at least some of the cell groups respectively taking intermediate results of cells of one or more other cell groups as input;

upon having calculated intermediate results for all cells of any one of the cell groups, marking these cells of said cell group as useless, for which the prospective final alignment score does not improve the current optimal alignment boundary threshold;

upon starting the calculation of any one of the cell groups, checking if all cells providing input to said one cell group are marked as useless cells; and aborting the calculation of any one of the cell groups in case the checking returned as result that all the cells providing input to said cell group are marked as useless and marking at least those cells in the cell group aborting its execution as useless, which are operable to provide input to another cell group.

* * * * *